US008936791B2

(12) United States Patent
Badiou et al.

(10) Patent No.: US 8,936,791 B2
(45) Date of Patent: Jan. 20, 2015

(54) **METHOD FOR IN VITRO DIAGNOSIS OF PVL-PRODUCING *STAPHYLOCOCCUS AUREUS***

(75) Inventors: Cedric Badiou, Bron (FR); Jerome Etienne, Caluire (FR); Gerard Lina, Lyons (FR); Catherine Ratat, Lyons (FR)

(73) Assignees: Biomerieux, Marcy l'Etoile (FR); Intstitut National de la Sante et de la Recherche Medicale (Inserm), Paris (FR); Universite Claude Bernard Lyon 1 (UCBL), Villeurbanne (FR)

( * ) Notice: Subject to any disclaimer, the term of this patent is extended or adjusted under 35 U.S.C. 154(b) by 390 days.

(21) Appl. No.: 12/311,160

(22) PCT Filed: Oct. 16, 2007

(86) PCT No.: PCT/FR2007/052165
§ 371 (c)(1),
(2), (4) Date: Mar. 20, 2009

(87) PCT Pub. No.: WO2008/050041
PCT Pub. Date: May 2, 2008

(65) Prior Publication Data
US 2010/0129839 A1      May 27, 2010

(30) Foreign Application Priority Data

Oct. 18, 2006  (FR) .................................... 06 54336
Feb. 6, 2007   (FR) .................................... 07 53081

(51) Int. Cl.
*A61K 39/085* (2006.01)
*A61K 39/02* (2006.01)
*G01N 33/53* (2006.01)
*G01N 33/569* (2006.01)

(52) U.S. Cl.
CPC ................................ *G01N 33/56938* (2013.01)
USPC .................. 424/243.1; 424/234.1; 424/236.1; 424/237.1; 435/4; 435/7.1

(58) Field of Classification Search
None
See application file for complete search history.

(56) References Cited

U.S. PATENT DOCUMENTS 4,647,654 A    3/1987  Knowles et al.
5,356,778 A   10/1994  Hansen et al.
5,904,922 A *  5/1999  Carroll ........................ 424/130.1

FOREIGN PATENT DOCUMENTS

EP       0 597 110 A1    5/1994
JP       B2-07-023891    3/1995
JP       A-10-078382     3/1998
WO       WO 2006/135912 A2  12/2006

OTHER PUBLICATIONS

Loeffler et al. J. Clin. Microbiol. 26: 1331-1334, 1988.*
Harlow and Lane In: Antibodies: A Laboratory Manual, Cold Spring Harbor Laboratory, p. 684, 1988.*
Western Blot Procedure, 2010.*
Thirunavukarasu et al. Prenatal Diagnosis 21: 638-641, 2001.*
Ward et al., "Identification of Staphylococcal Panton-Valentine Leukocidin as a Potent Dermonecrotic Toxin," *Infection and Immunity*, vol. 27, No. 5, May 1980, pp. 393-397.
Vandenesch et al., "Community-Acquired Methicillin-Resistant *Staphylococcus aureus* Carrying Panton-Valentine Leukocidin Genes: Worldwide Emergence," *Emerging Infectious Diseases*, vol. 9, No. 8, Aug. 2003, pp. 978-984.
Dufour et al., "Community-Acquired Methicillin-Resistant *Staphylococcus aureus* Infections in France: Emergence of a Single Clone That Produces Panton-Valentine Leukocidin," *Clinical Infectious Diseases*, vol. 35, Oct. 1, 2002, pp. 819-824.
Cribier et al., "*Staphylococcus aureus* Leukocidin: A New Virulence Factor in Cutaneous Infections? An Epidemiological and Experimental Study," *Dermatology*, vol. 185, 1992, pp. 175-180.
Freney et al., *Précis de Bactériologie Clinique* [Handbook of Clinical Bacteriology], vol. 40, p. 298, 2000.
Freney et al., *Précis de Bactériologie Clinique* [Handbook of Clinical Bacteriology], vol. 40, pp. 793-794, 2000.
Labandeira-Rey et al., "*Staphylococcus aureus* Panton-Valentine Leukocidin Causes Necrotizing Pneumonia," *Science*, vol. 315, Feb. 23, 2007, pp. 130-133.
Maltezou et al., "Community-acquired methicillin-resistant *Staphylococcus aureus* infections," *International Journal of Antimicrobial Agents*, vol. 27, No. 2, 2006, pp. 87-96.
Kasai et al., "Immunoassay of the MRSA-Related Toxic Protein, Leukocidin, with Scanning Electrochemical Microscopy," *Analytical Chemistry*, vol. 72, No. 23, Dec. 1, 2000, pp. 5761-5765.
Finck-Barbancon et al.; "Improved purification of leukocidin from *Staphylococcus aureus* and toxin distribution among hospital strains;" *Res. Microbiol.* (1991), vol. 142, pp. 75-85.

* cited by examiner

*Primary Examiner* — Rodney P Swartz
(74) *Attorney, Agent, or Firm* — Oliff PLC

(57) ABSTRACT

A method for in vitro diagnosis of *Staphylococcus aureus* producing Panton-Valentine Leukocidin (PVL), using a biological sample derived from an individual liable to be colonized by or infected with *Staphylococcus aureus*, wherein the diagnosis is carried out by detection of PVL using a routine immunological test, and the biological sample is pretreated in order to denature the PVL.

23 Claims, 3 Drawing Sheets

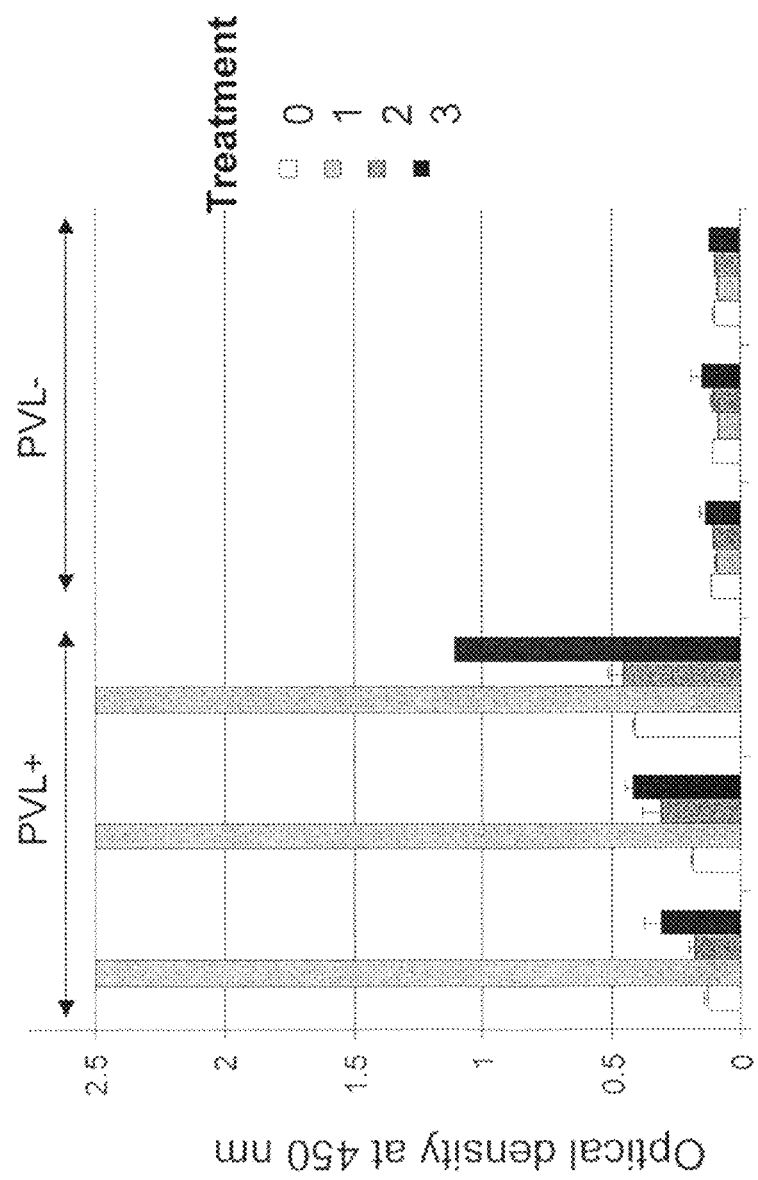

SEQUENCE LISTING

```
<160> NUMBER OF SEQ ID NOS: 4

<210> SEQ ID NO 1
<211> LENGTH: 309
<212> TYPE: PRT
<213> ORGANISM: Staphylococcus aureus

<400> SEQUENCE: 1

Met Ser Gly Ser His His His His His His Ser Ser Gly Ile Glu Gly
1               5                   10                  15

Arg Gly Arg Leu Ile Lys Ser Lys Ala Asp Asn Asn Ile Glu Asn Ile
            20                  25                  30

Gly Asp Gly Ala Glu Val Val Lys Arg Thr Glu Asp Thr Ser Ser Asp
        35                  40                  45

Lys Trp Gly Val Thr Gln Asn Ile Gln Phe Asp Phe Val Lys Asp Lys
50                  55                  60

Lys Tyr Asn Lys Asp Ala Leu Ile Leu Lys Met Gln Gly Phe Ile Asn
65                  70                  75                  80

Ser Lys Thr Thr Tyr Tyr Asn Tyr Lys Asn Thr Asp His Ile Lys Ala
            85                  90                  95

Met Arg Trp Pro Phe Gln Tyr Asn Ile Gly Leu Lys Thr Asn Asp Pro
            100                 105                 110

Asn Val Asp Leu Ile Asn Tyr Leu Pro Lys Asn Lys Ile Asp Ser Val
            115                 120                 125

Asn Val Ser Gln Thr Leu Gly Tyr Asn Ile Gly Gly Asn Phe Asn Ser
    130                 135                 140

Gly Pro Ser Thr Gly Gly Asn Gly Ser Phe Asn Tyr Ser Lys Thr Ile
145                 150                 155                 160

Ser Tyr Asn Gln Gln Asn Tyr Ile Ser Glu Val Glu His Gln Asn Ser
                165                 170                 175

Lys Ser Val Gln Trp Gly Ile Lys Ala Asn Ser Phe Ile Thr Ser Leu
            180                 185                 190

Gly Lys Met Ser Gly His Asp Pro Asn Leu Phe Val Gly Tyr Lys Pro
            195                 200                 205

Tyr Ser Gln Asn Pro Arg Asp Tyr Phe Val Pro Asp Asn Glu Leu Pro
210                 215                 220

Pro Leu Val His Ser Gly Phe Asn Pro Ser Phe Ile Ala Thr Val Ser
225                 230                 235                 240

His Glu Lys Gly Ser Gly Asp Thr Ser Glu Phe Glu Ile Thr Tyr Gly
                245                 250                 255

Arg Asn Met Asp Val Thr His Ala Thr Arg Arg Thr Thr His Tyr Gly
            260                 265                 270

Asn Ser Tyr Leu Glu Gly Ser Arg Ile His Asn Ala Phe Val Asn Arg
        275                 280                 285

Asn Tyr Thr Val Lys Tyr Glu Val Asn Trp Lys Thr His Glu Ile Lys
        290                 295                 300

Val Lys Gly His Asn
305
```

```
<210> SEQ ID NO 2
<211> LENGTH: 323
<212> TYPE: PRT
<213> ORGANISM: Staphylococcus aureus

<400> SEQUENCE: 2

Met Ser Gly Ser His His His His His His Ser Ser Gly Ile Glu Gly
1               5                   10                  15

Arg Gly Arg Leu Ile Lys Ala Gln His Ile Thr Pro Val Ser Glu Lys
            20                  25                  30

Lys Val Asp Asp Lys Ile Thr Leu Tyr Lys Thr Thr Ala Thr Ser Asp
        35                  40                  45

Ser Asp Lys Leu Lys Ile Ser Gln Ile Leu Thr Phe Asn Phe Ile Lys
    50                  55                  60

Asp Lys Ser Tyr Asp Lys Asp Thr Leu Ile Leu Lys Ala Ala Gly Asn
65                  70                  75                  80

Ile Tyr Ser Gly Tyr Thr Lys Pro Asn Pro Lys Asp Thr Ile Ser Ser
                85                  90                  95

Gln Phe Tyr Trp Gly Ser Lys Tyr Asn Ile Ser Ile Asn Ser Asp Ser
            100                 105                 110

Asn Asp Ser Val Asn Val Val Asp Tyr Ala Pro Lys Asn Gln Asn Glu
        115                 120                 125

Glu Phe Gln Val Gln Gln Thr Val Gly Tyr Ser Tyr Gly Gly Asp Ile
    130                 135                 140

Asn Ile Ser Asn Gly Leu Ser Gly Gly Gly Asn Gly Ser Lys Ser Phe
145                 150                 155                 160

Ser Glu Thr Ile Asn Tyr Lys Gln Glu Ser Tyr Arg Thr Ser Leu Asp
                165                 170                 175

Lys Arg Thr Asn Phe Lys Lys Ile Gly Trp Asp Val Glu Ala His Lys
            180                 185                 190

Ile Met Asn Asn Gly Trp Gly Pro Tyr Gly Arg Asp Ser Tyr His Ser
        195                 200                 205

Thr Tyr Gly Asn Glu Met Phe Leu Gly Ser Arg Gln Ser Asn Leu Asn
    210                 215                 220

Ala Gly Gln Asn Phe Leu Glu Tyr His Lys Met Pro Val Leu Ser Arg
225                 230                 235                 240

Gly Asn Phe Asn Pro Glu Phe Ile Gly Val Leu Ser Arg Lys Gln Asn
                245                 250                 255

Ala Ala Lys Lys Ser Lys Ile Thr Val Thr Tyr Gln Arg Glu Met Asp
            260                 265                 270

Arg Tyr Thr Asn Phe Trp Asn Gln Leu His Trp Ile Gly Asn Asn Tyr
        275                 280                 285

Lys Asp Glu Asn Arg Ala Thr His Thr Ser Ile Tyr Glu Val Asp Trp
    290                 295                 300

Glu Asn His Thr Val Lys Leu Ile Asp Thr Gln Ser Lys Glu Lys Asn
305                 310                 315                 320

Pro Met Ser

<210> SEQ ID NO 3
<211> LENGTH: 18
<212> TYPE: PRT
<213> ORGANISM: Staphylococcus aureus

<400> SEQUENCE: 3

Cys Ser Gly His Asp Pro Asn Leu Phe Val Gly Tyr Lys Pro Tyr Ser
1               5                   10                  15
```

```
Gln Asn

<210> SEQ ID NO 4
<211> LENGTH: 20
<212> TYPE: PRT
<213> ORGANISM: Staphylococcus aureus

<400> SEQUENCE: 4

Cys Asn Phe Asn Trp Ile Gly Asn Asn Tyr Lys Asp Glu Asn Arg Ala
1               5                   10                  15

Thr His Thr Ser
            20
```

METHOD FOR IN VITRO DIAGNOSIS OF PVL-PRODUCING *STAPHYLOCOCCUS AUREUS*

Figure 1:
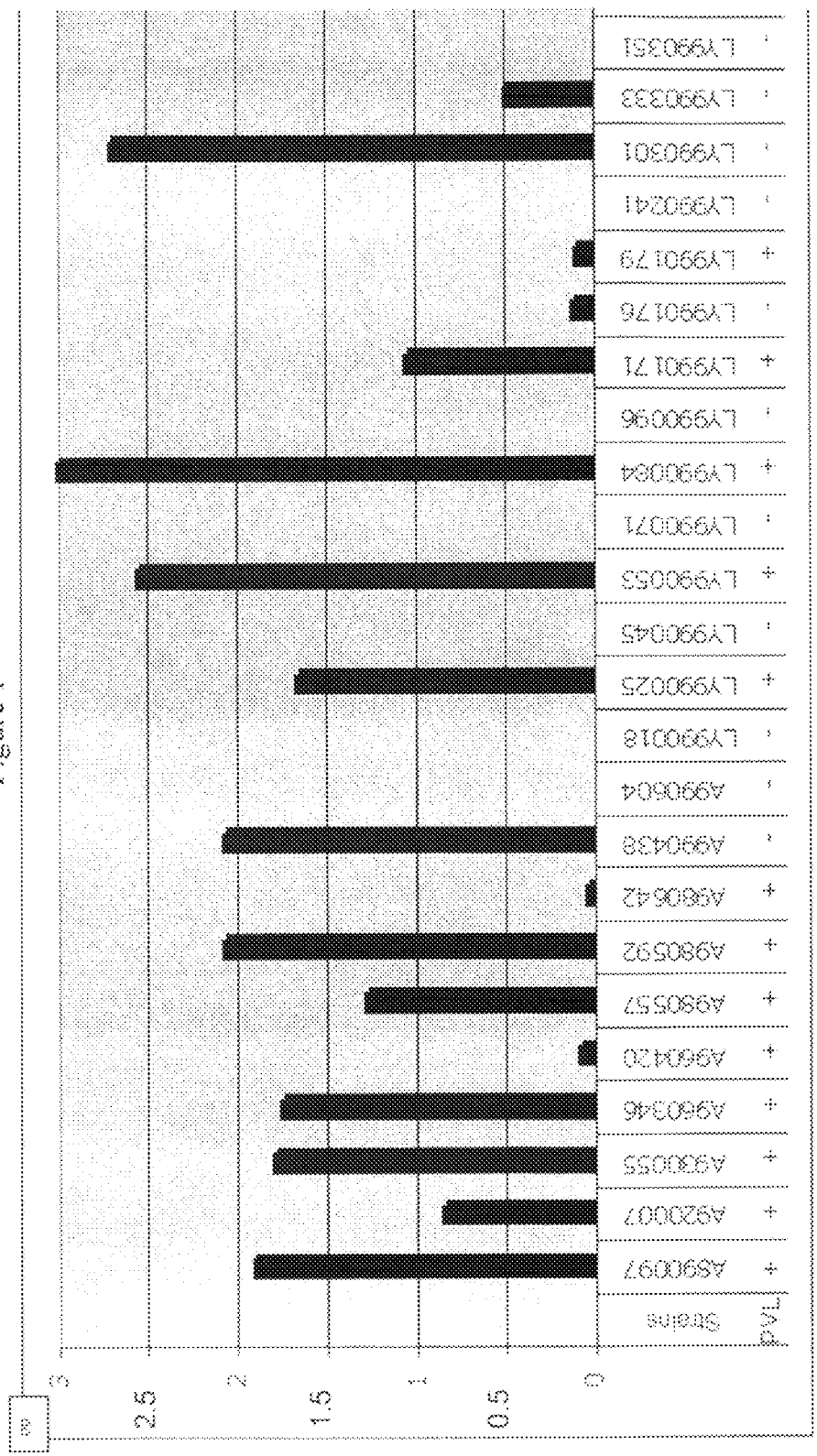

This is a national stage application filed under 35 U.S.C. §371 of PCT/FR2007/052165, filed Oct. 16, 2006, which claims the benefit of foreign applications FR 0753081, filed Feb. 6, 2007, and FR 0654336, filed Oct. 18, 2006. The disclosures of the prior applications are hereby incorporated by reference herein in their entirety.

The present invention relates to the field of infections associated with the presence of bacteria belonging to the *Staphylococcus* genus and of the species *Staphylococcus aureus*, which produce Panton-Valentine Leukocidin (PVL). More particularly, the subject of the present invention is a method for determining PVL-producing *Staphylococcus aureus* using a routine immunological test in a biological sample that may contain *Staphylococcus aureus*.

BACKGROUND

Infections with PVL-producing *Staphylococcus aureus* are essentially responsible for community infections. *Staphylococcus aureus* expresses a large variety of virulence factors, among which is Panton-Valentine Leukocidin (PVL), a cytotoxin which promotes tissue damage[1]. PVL is a toxin commonly present in community acquired methicillin-resistant *Staphylococcus aureus* (CA-MRSA) strains which are spreading worldwide[2].

PVL, and also other leukocidins, is a protein belonging to the family of synergohymenotropic toxins. All the toxins of this family are constituted of two polypeptide components, with synergic action, denoted S and F. PVL is encoded by two cotranscribed contiguous genes, lukF-PV and lukS-PV. PVL is an exotoxin since it is excreted into the extracellular medium whether or not there has been lysis of the bacterium, unlike endotoxins or lipopolysaccharides, which, themselves, are released only when the Gram-bacterium which secretes them has been destroyed.

PVL-producing *Staphylococcus aureus*, which are Gram+ bacteria, are associated with specific human infections such as cutaneous infections or subcutaneous infections, of the boil, abscess, cellulitis and myositis type, osteoarticular infections, and also severe necrotizing pneumonias which affect mainly children and young adults with a mortality rate of approximately 70%.

The pathogenesis is not completely known, but several lines of evidence suggest that PVL plays an important role in the physiopathology of infections with PVL-producing *Staphylococcus aureus*:
 i) the strong epidemiological link with isolates of *S. aureus* which synthesize PVL and the clinical presentation of the infection,
 ii) the high frequency of leukopenia, a known effect of PVL,
 iii) the necrotic lesions of the respiratory tract, resembling the necrosis induced by intradermal injection of PVL in rabbits,
 iv) the presence of PVL in the lungs targeting the polymorphonuclear cells,
 v) only PVL-producing strains or purified PVL induce necrotizing pneumonia in experimental models[7].

PVL-producing *S. aureus* are currently detected using tests for detecting nucleic acids, and in particular by detecting the lukF-PV and lukS-PV genes by PCR[3].

Such tests have the drawbacks that they are indirect since they do not make it possible to confirm that the gene is functional and/or expressed, they are expensive owing to the need for specific equipment, they are not very fast and they are difficult to carry out. In addition, in the context of the use of a PCR, contamination problems may occur.

The detection of PVL has also been carried out, from time to time, by immunodiffusion using polyclonal antibodies[4], but this technique was quickly abandoned in favor of the detection of genes since it is not very easy to carry out and difficult to standardize, such that it does not constitute a good tool for routine use.

Owing to the seriousness of certain infections due to PVL-producing *Staphylococcus aureus*, it is becoming urgent to have available a rapid test that is simple to carry out and that would overcome the drawbacks of the tests currently used to detect PVL-producing *S. aureus*.

Patent application EP 597 110 A describes the fact that the detection of MRSA can be carried out by means of routine immunological tests using anti-PVL monoclonal antibodies. However, although these tests make it possible to overcome the above drawbacks, the specificity of detection is not sufficient.

DETAILED DESCRIPTION

Against all expectations, the applicants have now demonstrated that the specificity of the detection of PVL-producing *S. aureus* using a routine immunological test can be improved by carrying out a pretreatment of the biological sample in order to denature the PVL, although it is known to those skilled in the art that, like any exotoxin, PVL is sensitive to physicochemical agents such as temperature[5].

Thus, the subject of the present invention is a method for in vitro diagnosis of *Staphylococcus aureus* producing Panton-Valentine Leukocidin (PVL) using a biological sample derived from an individual liable to be colonized by or infected with *Staphylococcus aureus*, wherein the diagnosis is carried out by detection of PVL using a routine immunological test, characterized in that said biological sample is pretreated in order to denature the PVL.

The expression "PVL-producing *Staphylococcus aureus*" is intended to mean all the *Staphylococcus aureus* strains capable of producing PVL, i.e. both the methicillin-sensitive strains (also known as MSSA), and those which are methicillin-resistant (also known as MRSA).

The expression "individual liable to be colonized by *Staphylococcus aureus*" is intended to mean the individuals at risk who may be healthy carriers of this bacterium, such as hospital staff. The expression "individual liable to be infected with *Staphylococcus aureus*" is intended to mean the patients displaying the symptoms of an infection with *Staphylococcus aureus*.

The expression "infection with *Staphylococcus aureus*" is intended to mean any infection caused by the presence of this bacterium in an organism, whether these infections are with PVL-producing *Staphylococcus aureus* or with *Staphylococcus aureus* which do not have such a capacity. By way of example of such infections, mention may be made of suppurative infections of the skin and of the soft tissues, respiratory tract infections, central nervous system infections, urinary infections, cardiac valve and endovascular infections and muscle and bone infections. Such infections and the associated symptoms are largely known to those skilled in the art and are described, in particular, in the Précis de Bactériologie Clinique[5] [Handbook of Clinical Bacteriology].

The expression "biological sample derived from an individual liable to be colonized by or infected with *Staphylococcus aureus*" is intended to mean any sample liable to contain these bacteria or else the excreted PVL, such as pus, a respiratory sample, a nasal sample, urine or a hemoculture.

The biological sample used in the method of the invention may be the unmodified sample, or else it may consist in a culture of the bacteria that is derived from this sample. The culture may be carried out on a solid medium, such as a Petri dish, or in a culture broth, it being understood that the culture broth can be inoculated with said sample or else with colonies of Staphylococcus aureus isolated beforehand from said biological sample by methods well known to those skilled in the art, such as by seeding on a Petri dish. The immunological test will then be carried out either directly on the solid medium, or in the culture broth. In general, the culturing of the bacteria of interest or of said sample lasts approximately 24 h. It may be noted that, whatever the culture, the culture medium comprises an agent for promoting the production of PVL, such as the CCY medium (casein hydrolyzate and yeast extract medium), with or without the use of molecules enabling a greater production of PVL, such as oxacillin and bactracin at a sub-inhibitory dose.

The term "immunological test" is intended to mean any immunological test using a binding partner capable of binding specifically to PVL, whether it is the LukF fraction of PVL, the LukS fraction of PVL, or else both fractions simultaneously.

The term "routine immunological test" is intended to mean any immunological test widely used in the routine practice of a laboratory. By way of example of routine immunological tests, mention may be made of sandwich tests of ELISA or immunochromatographic (also known as lateral flow) type, and particle, for example polystyrene particle, agglutination tests. All of these tests are widely known to those skilled in the art. The sandwich test can be carried out in one or more steps, i.e. without a washing step or with one or more washing steps.

By way of example of a PVL-specific binding partner, mention may be made of antibodies, antibody fractions, receptors, mimotopes and any other molecule capable of binding to PVL.

The binding-partner antibodies are, for example, either polyclonal antibodies or monoclonal antibodies.

The polyclonal antibodies can be obtained by immunization of an animal with PVL, a PVL fraction or a PVL peptide, followed by recovery of the serum of said animal. The antibodies can be used purified or nonpurified, in the method of the invention. The purification of the polyclonal antibodies can be carried out, for example, by taking the serum of said animal and separating said antibodies from the other serum constituents, in particular by affinity chromatography on a column to which an antigen specifically recognized by the antibodies, in particular PVL, is attached.

The monoclonal antibodies can be obtained by the hybridoma technique, the general principle of which is summarized hereinafter.

In a first step, an animal, generally a mouse (or cells in culture in the context of in vitro immunization), is immunized with PVL, a PVL fraction or a PVL peptide, and the B lymphocytes of this mouse are then capable of producing antibodies against said antigen. These antibody-producing lymphocytes are subsequently fused with "immortal" myeloma cells (murines in the example) so as to produce hybridomas. The heterogeneous mixture of the cells thus obtained is then used to form a selection of the cells capable of producing a particular antibody and of multiplying indefinitely. Each hybridoma is multiplied in the form of a clone, each one resulting in the production of a monoclonal antibody specifically recognizing PVL. The antibodies may be used purified or nonpurified in the method of the invention. The monoclonal antibodies may be purified in particular according to the affinity chromatography technique described above.

The monoclonal antibodies may also be recombinant antibodies obtained by genetic engineering, using techniques well known to those skilled in the art.

The expression "antibody fragments useful for the purposes of the invention" is intended to mean fragments of F(ab')2, Fab, Fab' or scFv type, of a native antibody, which have kept the capacity of specific binding to PVL.

The method of the invention is preferably carried out with the following characteristics, taken alone or in combination:

the routine immunological test is a sandwich method, it uses LukS-PV- or LukF-PV-specific binding partner(s), it uses antibody fragments, and in particular the F(ab')2 fragment.

In the context of a sandwich test using two PVL-specific binding partners, use may, for example, be made of two monoclonal antibodies, two polyclonal antibodies, or fragments thereof, or else one monoclonal antibody and one polyclonal antibody, or fragments thereof. In the context of a particle agglutination test, a single PVL-specific binding partner is used, for example either a monoclonal antibody or a polyclonal antibody, which may or may not be in the form of a fragment.

According to one particular embodiment, the immunological test uses at least one anti-PVL monoclonal antibody.

In the context of a particle agglutination test, the PVL-specific binding partner is used in capture mode. In the context of a sandwich test, they are used in capture mode and in detection mode.

When the binding partner is used as a detection reagent, it is labeled in order to reveal the PVL/binding partner binding.

The term "labeling of binding partners" is intended to mean the attachment of a label capable of directly or indirectly generating a detectable signal. A nonlimiting list of these labels comprises:

enzymes which produce a signal detectable, for example, by colorimetry, fluorescence or luminescence, such as horseradish peroxidase, alkaline phosphatase, α-galactosidase or glucose-6-phosphate dehydrogenase, chromophores, such as fluorescent, luminescent or dye compounds, radioactive molecules, such as $^{32}$P, $^{35}$S or $^{125}$I, and fluorescent molecules, such as alexa or phycocyanins.

Indirect detection systems can also be used, for instance ligands capable of reacting with an anti-ligand. The ligand/anti-ligand pairs are well known to those skilled in the art, this being the case, for example, of the following pairs: biotin/streptavidin, hapten/antibody, antigen/antibody, peptide/antibody, sugar/lectin, polynucleotide/sequence complementary to the polynucleotide. In this case, it is the ligand which carries the binding partner. The anti-ligand may be detectable directly via the labels described in the preceding paragraph, or may itself be detectable via a ligand/anti-ligand.

These indirect detection systems may result, under certain conditions, in an amplification of the signal. This signal amplification technique is well known to those skilled in the art, and reference may be made to the article in J. Histochem. Cytochem[6]. 45: 481-491, 1997.

Depending on the type of labeling used, those skilled in the art will add reagents for visualizing the labeling.

In the case of "competition" methods, the PVL is labeled as described above for the binding partner.

The PVL-specific binding partner, if it is used in the capture mode, is then directly or indirectly immobilized on a solid phase using methods known to those skilled in the art.

The pretreatment of the sample used in the method of the invention may be any protein-denaturing treatment widely known to those skilled in the art. This treatment may be carried out, for example, by modification of the pH, by using chemical denaturing agents, such as urea, sodium dodecyl sulfate (SDS) or guanidinium ions, or else by heating the sample which contains the protein to be denatured.

According to one embodiment, the pretreatment of said sample consists in heating at a temperature of between 60 and 100° C. for a period of at least 10 min. Preferably, the heating is carried out at a temperature of between 80 and 100° C., more preferably between 90 and 100° C.

Of course, the pretreatment of the sample will be applied to the sample itself when the routine immunological test is carried out in said sample, or else it will be applied to the culture when the immunological test is carried out in said culture.

The method of the invention may also comprise an additional step of verifying the presence of Staphylococcus aureus in said biological sample, it being possible for this step to be carried out beforehand or concomitantly. The methods for detecting these bacteria are known to those skilled in the art, and mention may be made, by way of example, of the use of media containing a chromogenic agent specific for this bacterium, as described, for example, in patent application WO 02/079486 filed by one of the applicants.

Similarly, the method of the invention may comprise an additional step consisting in determining whether the Staphylococcus aureus present in said biological sample are methicillin-resistant (MRSA) or methicillin-sensitive (MSSA) bacteria, thereby constituting a particular embodiment of the invention.

This step of determining the methicillin sensitivity (MRSA or MSSA) can be carried out by methods widely known to those skilled in the art, such as immunological tests using, for example, a binding partner specific to the PBP2' protein, which is a protein expressed only by MRSA, tests for detecting nucleic acid or else microbiological tests, for example using a medium containing an antibiotic such as oxacillin or a cephalosporin, for example cefoxitin.

Figure 2:
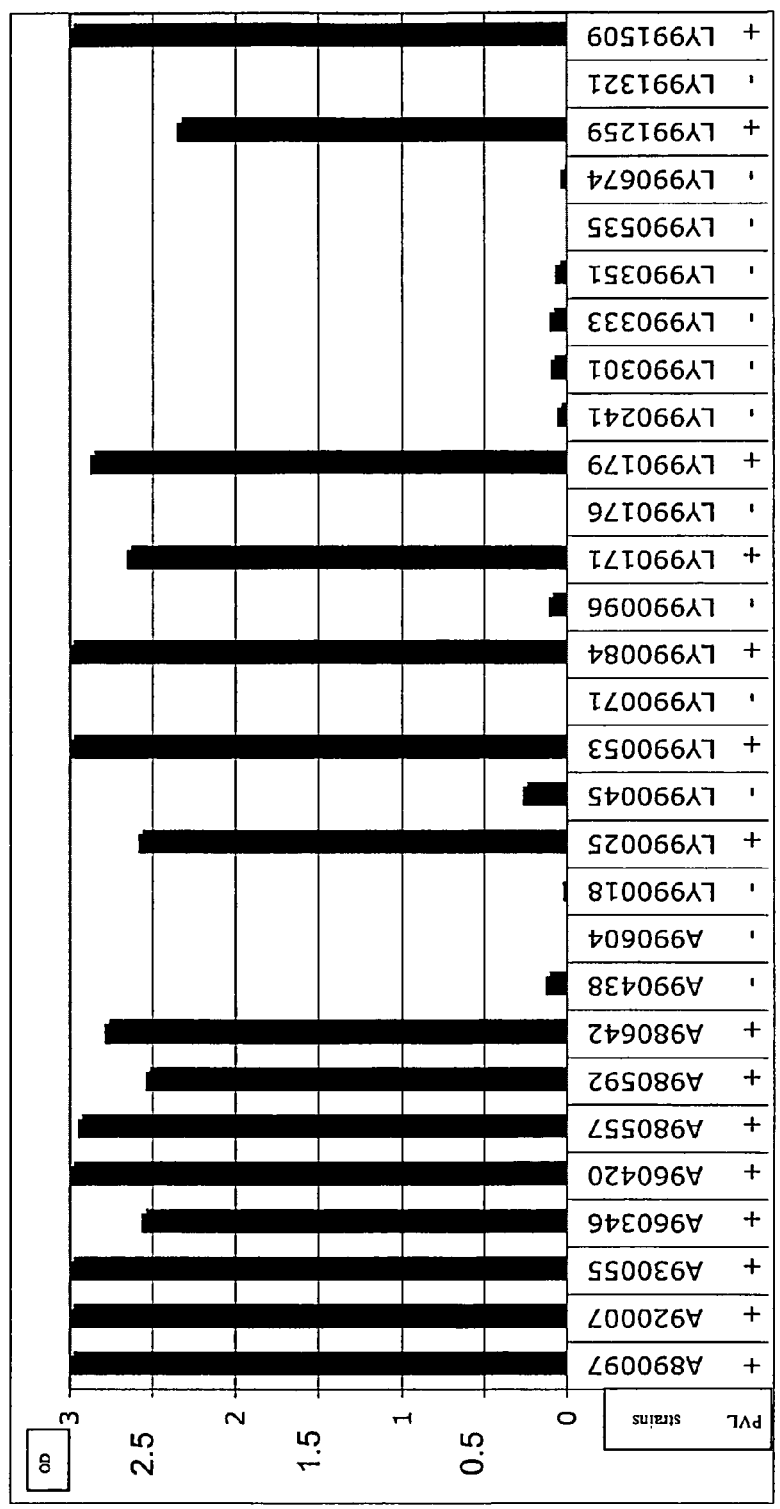

The invention will be understood more clearly by means of the following examples given by way of nonlimiting illustration, and also by means of the attached FIGS. 1 to 3, in which:

FIG. 1 is a graph giving the results of an ELISA test (OD of each strain) for the detection of PVL in biological samples containing strains of Staphylococcus aureus producing PVL (PVL+) or not producing PVL (PVL−), FIG. 2 is a graph giving the results of an ELISA test (OD of each strain) for the detection of PVL in biological samples containing strains of Staphylococcus aureus producing PVL (PVL+) or not producing PVL (PVL−), said sample having been pretreated by heating in order to denature the PVL, and FIG. 3 is a graph giving the results of an ELISA test (OD of each strain) for the detection of PVL in biological samples containing strains of Staphylococcus aureus producing PVL (LY990084, A92007, LUG855) or not producing PVL (LY990333, LY991321, RN6911), said sample having been pretreated by heating (treatment 1), pretreated using a chemical denaturing agent (treatment 2), or pretreated using a denaturing agent and by heating (treatment 3), state 0 corresponding to no pretreatment of the sample.

Example 1

Preparation of Anti-PVL Antibodies

1. Production of Recombinant PVL

The LukS His-Tag and LukF His-Tag proteins of respective sequence SEQ ID No. 1 and SEQ ID No. 2 were produced using the vector pIVEX 2.4d (Roche) used to transform a strain of Escherichia coli BL21star(DE3) pLys (Invitrogen) during culturing of 2 liters at 37° C. with shaking, induction for 3 h at 37° C. with 1 mM IPTG (isopropyl-beta-D-thiogalactopyranoside, Eurobio), and then culturing for a further 5 hours. The culture is dispensed into 6 different tubes.

Each cell pellet is recovered by centrifugation at 4000 g for 20 min and removal of the supernatant. The recombinant proteins are purified using the QIAexpressionist kit according to the recommendations of the supplier (Qiagen). The pellet is lyzed with 20 ml of a nondenaturing lysis solution (Qiagen) at 4° C., and then conserved overnight at −80° C. After thawing, the lysis is continued using a treatment with lysozyme (Eurobio) 1 mg/ml for 1 h at 4° C., before sonication using a VIBRACELL (Bioblock) at 100 watt, for 2 min in cycles of 6 s.

The solution is centrifuged at 10 000 g for 30 min at 4° C. The supernatant is brought into contact with 5 ml of agarose-NiNTA (Qiagen) for 3 h at 4° C. with gentle circular agitation. The agarose is then placed in a 20 ml column (Biorad). The column is washed with 200 ml of wash buffer (Qiagen), and then eluted with 250 mM imidazole as eluting buffer. This purification is completed by purification on a monoSP ion exchange column (Amersham).

The recombinant proteins are concentrated on a CENTRICON (Vivaspin), dialyzed against a 50 mM MES (2-(N-morpholino)ethanesulfonic acid) buffer, and then eluted with a gradient of NaCl (0 to 1M). The proteins are then dialyzed against apyrogenic sterile water.

2. Production of Monoclonal Antibodies

The following monoclonal antibodies were obtained:
anti-LukF: 10D1A10, 16A10A3, 6H10 E5 and
anti-LukS: 2H2H12, 3D9D12, 7C1F9, 7F8D7, 18A4E10
as follows:

Ant-Luk F Monoclonal Antibodies: 10D1A10, 16A10A3, 6H10E5.

The mice were immunized according to the following protocol: at day D0, intraperitoneal injection of 10 µg of recombinant Luk F protein in the presence of complete Freund's adjuvant. At days D14, D28, further intraperitoneal injection of the same amount of recombinant Luk F protein in the presence of incomplete Freund's adjuvant. Four days before the fusion, an intravenous injection of 50 µg of Luk F antigen diluted in physiological saline is given.

1600 supernatants were screened by the indirect ELISA technique. The plates were "coated" with 100 µl of antigen (recombinant Luk F protein) at 1 µg/ml in PBS buffer, pH 7.2. The "coated" plates were incubated overnight at the temperature of 18-22° C. The plates were saturated with 200 µl of PBS-1% milk and subjected to incubation for 1 hour at 37°+/− 2° C. 100 µl of supernatants or of ascites fluid diluted in PBS buffer-0.05% TWEEN 20, were added and the plates were incubated for 1 hour at 37°±/2° C. 100 µl of goat anti-mouse Ig(H+L) polyclonal antibody conjugated to alkaline phosphatase (Jackson Immunoresearch ref:115-055-062), diluted to 1/2000 in PBS buffer-1% BSA, were added and the plates were subsequently incubated for 1 hour at 37°±/2° C. 100 µl of PNPP (bioMérieux ref. 60002990) at the concentration of 2 mg/ml in DEA-HCl (bioMérieux ref. 60002989), pH=9.8, were added. The plates were subjected to incubation for 30 minutes at 37°±/−2° C. The reaction was blocked by adding 100 µl of 1N NaOH. Three washes are carried out between each step, with 300 µl of PBS-0.05% tween 20. A further wash in distilled water is carried out before adding the PNPP.

72 supernatants were found to be positive by indirect ELISA with an OD>0.6. After the specificity test, the above-mentioned three antibodies are produced.

Anti-Luk S Monoclonal Antibodies: 2H2H12, 3D9D12, 7C1F9, 7F8D7, 18A4E10

The mice were immunized according to the following protocol: at day D0, intraperitoneal injection of 10 µg of recombinant Luk S protein in the presence of complete Freund's adjuvant. At days D14, D28, a further intraperitoneal injection of the same amount of recombinant LuK S protein in the presence of incomplete Freund's adjuvant. Four days before the fusion, an intravenous injection of 50 µg of recombinant Luk S protein, diluted in physiological saline, is given.

1800 supernatants were screened by the indirect ELISA technique. The plates were "coated" with 100 µl of recombinant Luk S protein at 1 µg/ml in PBS buffer, pH 7.2. The "coated" plates were incubated overnight at a temperature of 18-22° C. The plates were saturated with 200 µl of PBS-1% milk and subjected to incubation for 1 hour at 37°±/−2° C. 100 µl of supernatants or of ascites fluid, diluted in PBS buffer-0.05% TWEEN 20, were added and the plates were incubated for 1 hour at 37°±/−2° C. 100 µl of goat anti-mouse Ig(H+L) polyclonal antibody conjugated to alkaline phosphatase (Jackson Immunoresearch ref.: 115-055-062), diluted to 1/2000 in PBS buffer-1% BSA, were added and the plates were then incubated for 1 hour at 37°±/−2° C. 100 µl of PNPP (Biomérieux ref. 60002990) at the concentration of 2 mg/ml in DEA-HCl (Biomérieux ref. 60002989), pH=9.8, were added. The plates were subjected to incubation for 30 minutes at 37°±/−2° C. The reaction was blocked by adding 100 µl of 1N NaOH. Three washes are carried out between each step, with 300 µl of PBS-0.05% TWEEN 20. A further wash in distilled water is carried out before adding the PNPP.

51 supernatants were found to be positive by indirect ELISA with an OD>0.6. After the specificity tests, the above-mentioned five antibodies are produced.

3. Production of Polyclonal Antibodies 3.1. Production of Anti-Luk S Polyclonal Antibodies The anti-LukS polyclonal antibodies No. 173/89 and 176/89 were obtained as follows:

At day D0, rabbits (New Zealand White) received an intradermal injection of 200 µg of LukS-PV synthetic peptide of sequence CSGHDPNLFVGYKPYSQN (SEQ ID No. 3), N-terminal coupled with KLH (Keyhole Limpet Hemocyanin) (Agro-Bio). At days D14, D28, D42 and D81, the rabbits received a further subcutaneous injection of the same amount of synthetic peptide coupled to KLH. The serum of the animals is taken at D0, D49 and D89. The rabbit sera taken at D89 are purified by affinity chromatography on said synthetic peptide. For this, said peptide is coupled onto a 1 ml HI-TRAP SEPHAROSE column according to the recommendations of the manufacturer (Amersham-Pharmacia). The serum is diluted 50/50 in PBS buffer, pH 7.4, and then injected onto the column at a rate of 1 ml/min. After washing with PBS, pH 7.4, and then elution with 50 mM of glycine/HCl mixture, pH 3, the eluted fractions are immediately neutralized, and then dialyzed against 0.15 M PBS, pH 7.4.

3.2. Production of Anti-Luk F Polyclonal Antibodies

The anti-LukF polyclonal antibodies were obtained as follows:

At day D0, rabbits (New Zealand White) received an intradermal injection of 200 mg of LukF-PV synthetic peptide of sequence CNFNWIGNNYKDENRATHTS (SEQ ID No. 4), N terminal coupled with KLH (Keyhole Limpet Hemocyanin) (Agro-Bio). At days D14, D28, D42 and D81, the rabbits received a further subcutaneous injection of the same amount of synthetic peptide coupled to KLH. The serum of the animals is taken at D0, D49 and D89. The rabbit sera taken at D89 are purified by affinity chromatography on said synthetic peptide. For this, said peptide is coupled onto a 1 ml HI-TRAP SEPHAROSE column according to the recommendations of the manufacturer (Amersham-Pharmacia). The serum is diluted 50/50 in PBS buffer, pH 7.4, and then injected onto the column at a rate of 1 ml/min. After washing with PBS, pH 7.4, and then elution with 50 mM of glycine/HCl mixture, pH 3, the eluted fractions are immediately neutralized, and then dialyzed against 0.15M PBS, pH 7.4.

4. Production and Coupling of Antibody Fragments

The anti-LukS polyclonal antibodies 173/89 and 176/89 were digested with pepsin bound to agarose, for 1 h 30 at pH 3.5 at 37° C., in order to eliminate the Fc fragment thereof and thus to obtain the F(ab')2 fragments.

These fragments were labeled with peroxidase as follows: the F(ab')2 fragments are dialyzed against carbonate buffer, pH 9.6, and coupled to peroxidase (Roche) oxidized beforehand with $NaIO_4$, for 2 hours at 18-25° C. with a ratio of: 1 mol of F(ab')2 per 2 mol of peroxidase. The coupling is then blocked with $NaBH_4$ for 1 hour at 2-8° C., and the product is then dialyzed against PBS buffer with preservatives.

They were subsequently labeled with biotin as follows: the F(ab')2 fragments are dialyzed against carbonate buffer, pH 8.3, and coupled to biotin-NHS (Roche) for 1 hour at 18-25° C. with a ratio of 1 mol of F(ab')2 per 10 mol of biotin. The coupling is blocked with lysine for 20 minutes at 18-25° C., and the product is then dialyzed against PBS+azide.

Example 2

Diagnosis of PVL-Producing *Staphylococcus aureus* Strains

1. Preparation of the Biological Sample

The clinical strains of *Staphylococcus aureus* are precultured on GP agar (Difco: 10 g/l peptone, 5 g/l yeast extract, 17 g/l agar; Sigma: 5 g/l NaCl, 1 g/l glucose). After 18 h at 37° C., the purity is verified before inoculating some colonies (approximately $10^7$ CFU/ml) into 5 ml of CCY medium (Difco: 30 g/l yeast extract, 20 g/l casamino acid; Sigma: 3.11 g/l $Na_2HPO_4$ $2H_2O$, 0.41 g/l $KH_2PO_4$, 23 g/l pyruvic acid) in a 25 ml glass Erlenmeyer flask. After culturing for 18 h at 37° C. with shaking, the culture supernatants are recovered after centrifugation (8000 g, 4° C., 10 min), and are then conserved for a short period at 4° C. or at −20° C. before use.

Each strain was given an identifier (A or LY plus 6 numbers) and is denoted "+" if it produces PVL or "−" if it does not produce PVL.

2. ELISA Test

The ELISA plate wells (Greiner, 100 µl/well) are coated with anti-LukS antibody 18A4E10 by incubation with a solution of this antibody diluted to 10 µg/ml in PBS (Sigma PBS, pH 7.4; 0.1% sodium azide) for 18 h at ambient temperature (approximately 22° C.). After 5 washes in PBS TWEEN 20 (Biorad ImmunoWash 1575 machine), the plate is saturated with a solution of TWEEN 20 (0.05%)/10% milk/0.5% BSA (Sigma) for 2 h at ambient temperature (150 µl/well).

After 5 washes with PBS TWEEN (0.05%), the culture supernatants are incubated for 75 min at 37° C.

After 5 washes with PBS TWEEN (0.05%), the solution of rabbit antibody 176-89, F(ab'2) fragment labeled with peroxidase, diluted to 1/100 in PBS-T 5% milk, is incubated for 75 min at 37° C. After 5 washes with PBS TWEEN, 75 μl of TMB solution (3,3',5,5'-tetramethylbenzine substrate, Sigma) are added and the plate is incubated for 30 min in the dark. The reaction is stopped by adding 75 μl of 1N $H_2SO_4$. The plates are read (OD) at 450 nm using the MicroPlate MP Reader 680 (Biorad).

3. Results

The results are shown in FIG. 1, which is a graph giving the OD of each strain.

The results show that, among the 15 PVL+ strains, 12 strains are clearly detected and that, among the 14 PVL− strains, 3 false-positive results are observed.

These results clearly show that it is possible to differentiate between the PVL+strains and the PVL− strains using a routine immunological test, but that the latter lacks specificity.

Example 3

Diagnosis of PVL-Producing *Staphylococcus aureus* Strains After Pretreatment of the Biological Sample by Heating 1. Treatment of the Sample The biological samples, as prepared in example 2, were treated by heating at 95° C. for periods of time ranging from 10 to 30 min, and their OD was determined according to the protocol described in example 2.

The OD results are given in table 1 below, which shows that denaturation of the PVL is obtained from 10 min of treatment onward.

TABLE 1

| Strain No. | PVL | No heating | Heating for 10 min | Heating for 20 min | Heating for 30 min |
|---|---|---|---|---|---|
| LY990179 | + | 0.839 | 2.126 | 2.76 | >3 |
| A960420 | + | 1.73 | 2.844 | >3 | >3 |
| A990438 | − | 1.545 | 0.852 | 0.25 | 0 |
| A980642 | + | 0.458 | 1.364 | 2.325 | >3 |
| LY990301 | − | 2.123 | 0.105 | 0 | 0 |
| HT20020275 | + | 0.729 | 2.269 | >3 | >3 |
| LY990333 | − | 0.615 | 0.202 | 0 | 0 |
| HT20040540 | + | 1.178 | >3 | >3 | >3 |

2. ELISA Test

The procedure described in example 2, point 2 above was repeated, except for the fact that the culture supernatants of 29 strains (15 PVL+ and 14 PVL−) pretreated at 95° C. for 1 h were used.

3. Results

The results are shown in FIG. 2, which is a graph giving the OD of each strain.

The results show that all the PVL+ strains are identified by the method of the invention, with an OD level that is sufficiently high to make a distinction with the PVL-strains.

The pretreatment therefore makes it possible to improve the specificity of the method of the invention.

Example 4

Diagnosis of PVL-Producing *Staphylococcus aureus* Strains after Pretreatment of the Biological Sample Using Several Types of Denaturing Treatment 1. Treatment of the Sample Three clinical PVL+ strains (LY990084, A92007, LUG855) and three clinical PVL− strains (LY990333, LY991321, RN6911) were used, and were subjected to the following treatments:

no treatment (0), denaturation by heating at 95° C. for 1 h (1), denaturation with acid, $KH_2PO_4$ final concentration of 0.1 M, for 30 min on a vortex, then neutralization by adding NaOH (2), mixed denaturation with acid, $KH_2PO_4$, final concentration of 0.1M, for 10 min on a vortex, then boiling for 10 min at 95° C., followed by neutralization with NaOH (3).

2. ELISA Test

The procedure described in example 2 was repeated, except for the fact that the strains pretreated according to point 1 above and a solution of rabbit antibody 176-89, F(ab'2) fragment labeled with peroxidase, diluted to 1/1000 in PBS-TWEEN 5% milk were used.

3. Results

The results are shown in FIG. 3, which is a graph giving the OD of each strain.

The results show that all the PVL− strains have OD values of between 0.09 and 0.181, whatever the treatment of the sample.

For the PVL+ strains, the OD values are higher than those of the PVL− strains after treatment. The increase in OD obtained by chemical treatment, by heat treatment and by a combination of the two is statistically significant (p=0.024, p<0.001, p=0.018, respectively), even though the heat treatment appears to be the most effective under these conditions.

The pretreatment therefore makes it possible to improve the specificity of a routine immunological test.

Example 5

Demonstration of the Early Detection of PVL-Producing *Staphylococcus aureus* Bacteria Using the Method of the Invention 1. Preparation of the Biological Sample Four clinical strains of *S. aureus* (2 PVL+ strains and 2 PVL− strains) were precultured according to the procedure described in example 2. The colonies are used to carry out a rich inoculation of 5 ml of CCY medium in a 25 ml glass Erlenmeyer flask. The culture medium is sampled immediately after inoculation, and then successively at 1 h, 2 h, 3 h and 18 h after incubation at 37° C. with shaking. The culture supernatants are recovered after centrifugation (8000 g, 4° C., 10 min), and are then conserved for a short period at 4° C. or at −20° C. before use. The samples are treated by heating as described in example 3.

2. ELISA Test

The procedure described in example 2, point 2 above was repeated, except for the fact that the culture supernatants of the strains pretreated as described in point 1 above were used.

3. Results

The OD results are given in table 2, which shows that the PVL can be detected very rapidly with the method of the invention (clear detection from 2 h of culture onward).

TABLE 2

| Strain No. | | Culture time | | | | |
|---|---|---|---|---|---|---|
| | | T0 | T1 h | T2 h | T3 h | T18 h |
| A89 0097 | PVL+ | 0.161 | 1.116 | >3 | >3 | >3 |
| A92 0007 | PVL+ | 0.083 | 0.975 | 2.57 | >3 | >3 |
| LY99 0301 | PVL− | 0 | 0 | 0 | 0 | 0 |
| LY99 0333 | PVL− | 0 | 0 | 0 | 0 | 0 |

Example 6

Demonstration of the Early Detection of PVL in Biological Specimens Using the Method of the Invention 1. Preparation of the Biological Sample The clinical specimens are bronchopulmonary aspirations, bronchoalveolar fluids and pus from skin abscesses or pus from a deep suppuration of patients having S. aureus infections with either PVL+ strains or PVL− strains. These specimens were conserved at −20° C. before being analyzed using the method of the invention. After thawing at ambient temperature, the specimens are homogenized by vortexing for 15 min. After centrifugation (10 min, at 4000 rpm at 15° C.), the supernatant is transferred into an Eppendorf tube, and then denatured for 1 h at 95° C.

For the very viscous samples, the samples are first diluted 50/50 with PBS, pH 7.4, and then vortexed for 15 min. After centrifugation (10 min, at 4000 rpm at 15° C.), the supernatant is transferred into an Eppendorf tube, and then denatured for 1 h at 95° C.

In the case of a viscous supernatant, the latter is diluted 50/50 with n-heptane (Merck), and again vortexed for 10 min. After centrifugation (10 min, at 4000 rpm at 15° C.), the upper phase corresponding to the n-heptane is completely removed and the lower phase is transferred into another Eppendorf tube in order to be denatured for 1 h at 95° C.

2. ELISA Test

The procedure described in example 2, point 2 above was repeated, except for the fact that the biological specimens treated as described in point 1 above were used.

3. Results

The PVL assay results are given in tables 3 and 4, which show that the PVL can be detected directly in the biological specimens, whatever the methicillin-sensitivity of the strain, and that there is no false positive (no sample having PVL− strains is detected as containing PVL). Moreover, the pretreatment of the specimen with n-heptane does not impair the detection of the PVL.

TABLE 3

| Specimen | Type of specimen | Specimen pretreatment | Strain* | Amount of PVL (µg/ml) |
|---|---|---|---|---|
| 17 | Bronchoalveolar lavage | no | PVL+ | <0.05 |
| 13 | Bronchial aspiration | no | PVL− | <0.05 |
| 18 | Bronchoalveolar mini lavage | no | PVL− | <0.05 |
| 22 | Bronchial aspiration | no | PVL− | <0.05 |
| 11 | Bronchial aspiration | no | PVL− | <0.05 |
| 8 | Bronchial aspiration | PBS + n-heptane | PVL− | <0.05 |
| 16 | Bronchial aspiration | no | PVL− | <0.05 |
| 10 | Bronchial aspiration | no | PVL− | <0.05 |
| 19 | Sputum | no | PVL− | <0.05 |
| 14 | Bronchial aspiration | no | PVL− | <0.05 |
| 15 | Bronchial aspiration | no | PVL− | <0.05 |
| 12 | Bronchial aspiration | no | PVL− | <0.05 |
| 7 | Bronchial aspiration | no | PVL− | <0.05 |
| 5 | Bronchial aspiration | no | PVL− | <0.05 |
| 23 | Joint fluid | no | PVL− | <0.05 |
| 20 | Peritoneal fluid | no | PVL− | <0.05 |
| 4 | Drain fluid | no | PVL+ | <0.05 |
| 2 | Abscess | no | PVL+ | 1 |
| 3 | Abscess | no | PVL− | <0.05 |
| 1 | Drain fluid | no | PVL− | <0.05 |
| 5 | Bronchial aspiration | PBS | PVL+ | 1.2 |
| 5 | Bronchial aspiration | PBS + n-heptane | PVL+ | 1.2 |
| 6 | Bronchial aspiration | PBS + n-heptane | PVL+ | 1.2 |

*The determination of whether the strain was PVL− or PVL+ was carried out by detection of the presence, by PCR, of the LukS-PV and LukF-PV genes encoding PVL within the S. aureus isolates according to the methods described by Vandenesch et al.[2]

TABLE 4

| | Sample | Strain* | Concentration of Luk S-PV (µg/ml) | Detection of mecA gene** |
|---|---|---|---|---|
| Pneumonia | Bronchoalveolar lavage | PVL+ | 0.99 | 0 |
| | Bronchoalveolar lavage | PVL+ | 1.07 | 0 |
| | Bronchoalveolar lavage | PVL+ | 20.18 | 0 |
| | Sputum | PVL− | 0.00 | 1 |
| | Sputum | PVL− | 0.00 | 1 |
| | Bronchoalveolar lavage | PVL− | 0.00 | 1 |
| | Sputum | PVL− | 0.00 | 1 |
| | Bronchoalveolar lavage | PVL− | 0.00 | ND |
| | Bronchial aspiration | PVL− | 0.00 | 0 |
| | Bronchial aspiration | PVL− | 0.00 | 0 |
| | Bronchial aspiration | PVL− | 0.00 | 0 |

TABLE 4-continued

|  | Sample | Strain* | Concentration of Luk S-PV (µg/ml) | Detection of mecA gene** |
|---|---|---|---|---|
|  | Bronchoalveolar lavage | PVL− | 0.00 | 0 |
|  | Bronchial aspiration | PVL− | 0.00 | 1 |
|  | Bronchial aspiration | PVL− | 0.00 | 0 |
|  | Bronchial aspiration | PVL− | 0.00 | 1 |
|  | Bronchial aspiration | PVL− | 0.00 | 0 |
|  | Bronchial aspiration | PVL− | 0.00 | 0 |
|  | Sputum | PVL− | 0.00 | 0 |
|  | Bronchial aspiration | PVL− | 0.00 | 0 |
|  | Bronchial aspiration | PVL− | 0.00 | 0 |
|  | Bronchial aspiration | PVL− | 0.00 | ND |
|  | Bronchial aspiration | PVL− | 0.00 | 1 |
|  | Bronchial aspiration | PVL− | 0.00 | 0 |
| Skin infection | Abscess | PVL+ | >1 | 0 |
|  | Abscess | PVL+ | 0.42 | 0 |
|  | Abscess | PVL+ | >1 | 1 |
|  | Abscess | PVL+ | >1 | 0 |
|  | Abscess | PVL+ | 1.20 | 0 |
|  | Abscess | PVL+ | 1.00 | 0 |
|  | Abscess | PVL+ | 1.30 | 0 |
|  | Abscess | PVL+ | 1.50 | 1 |
|  | Abscess | PVL+ | 1.82 | 0 |
|  | Abscess | PVL+ | >2 | 0 |
|  | Abscess | PVL+ | 0.92 | 0 |
|  | Abscess | PVL+ | >2 | 0 |
|  | Abscess | PVL+ | 0.27 | 0 |
|  | Abscess | PVL+ | >2 | 0 |
|  | Abscess | PVL+ | 1.72 | 0 |
|  | Abscess | PVL+ | 1.41 | 0 |
|  | Abscess | PVL− | 0.00 | 0 |
|  | Abscess | PVL− | 0.00 | 1 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 1 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 0 |
|  | Abscess | PVL− | 0.00 | 0 |

*The determination of whether the strain was PVL− or PVL+ was carried out by detection of the presence, by PCR, of the LukS-PV and LukF-PV genes encoding PVL within the S. aureus isolates according to the methods described by Vandenesch et al.[2]

**The detection of the mecA gene encoding the methicillin resistance within the S. aureus isolates was carried out according to the methods described by Vandenesch et al.[2]

LITERATURE

1: Ward P D, Turner W D, 1980, Infect. Immun., 28(2): 393-397
2: Vandenesch et al., 2003, Emerg Infect Dis, 9(8): 978-984
3: Dufour P et al., 2002, Clin Infect Dis, 35: 819-824
4: Cribier B et al, 1992, Dermatology, 185: 175-185
5: Freney J et al., 2000, Precis de Bactériologie Clinique [Handbook of clinical bacteriology], 40: 298 and 793-794
6: J. Histochem. Cytochem. 45: 481-491, 1997
7: Labandeira-Rey M et al, Science 2007, in press

The invention claimed is:

1. A method for in vitro detection of whether Panton-Valentine Leukocidin (PVL) is present in a biological sample from an individual liable to be colonized by or infected with PVL-producing *Staphylococcus aureus*, the method comprising:
   pretreating the biological sample to denature the PVL when present in the biological sample, the pretreatment comprising heating the biological sample at a temperature of between 60 and 100° C. for a period of more than 10 minutes; and
   detecting whether the PVL is present in the biological sample using an immunological test, the immunological test comprising an enzyme-linked immunosorbent assay (ELISA), lateral flow immunochromatography, or an agglutination test,
   wherein the detection of the PVL in the biological sample indicates that the individual is colonized by or infected with the PVL-producing *Staphylococcus aureus*.

2. The method as claimed in claim 1, wherein the immunological test is a lateral flow immunochromatography sandwich method.

3. The method as claimed in claim 1, wherein the immunological test uses at least one anti-PVL monoclonal antibody.

4. The method as claimed in claim 2, wherein the immunological test uses at least one anti-PVL monoclonal antibody.

5. The method as claimed in claim 1, further comprising determining whether the PVL-producing *Staphylococcus aureus* are methicillin-resistant (MRSA) or methicillin-sensitive (MSSA) when the PVL is detected in the biological sample.

6. The method as claimed in claim 2, further comprising determining whether the PVL-producing *Staphylococcus aureus* are methicillin-resistant (MRSA) or methicillin-sensitive (MSSA) when the PVL is detected in the biological sample.

7. The method as claimed in claim 3, further comprising determining whether the PVL-producing *Staphylococcus aureus* are methicillin-resistant (MRSA) or methicillin-sensitive (MSSA) when the PVL is detected in the biological sample.

8. The method as claimed in claim 4, further comprising determining whether the PVL-producing *Staphylococcus aureus* are methicillin-resistant (MRSA) or methicillin-sensitive (MSSA) when the PVL is detected in the biological sample.

9. The method as claimed in claim 1, wherein the pretreatment comprises heating at a temperature of between 60 and 100° C. for a period of 20 minutes or more.

10. The method as claimed in claim 1, wherein the pretreatment comprises heating at a temperature of between 60 and 100° C. for a period of from more than 10 minutes to 30 minutes.

11. A method for in vitro detection of whether Panton-Valentine Leukocidin (PVL) is present in a biological sample from an individual liable to be colonized by or infected with PVL-producing *Staphylococcus aureus*, the method comprising:
    pretreating the biological sample to denature the PVL when present in the biological sample, the pretreatment comprising using an acid; and
    detecting whether the PVL is present in the biological sample using an immunological test, the immunological test comprising an enzyme-linked immunosorbent assay (ELISA), lateral flow immunochromatography, or an agglutination test,
    wherein the detection of the PVL in the biological sample indicates that the individual is colonized by or infected with the PVL-producing *Staphylococcus aureus*.

12. The method as claimed in claim 11, wherein the immunological test is a lateral flow immunochromatography sandwich method.

13. The method as claimed in claim 11, wherein the immunological test uses at least one anti-PVL monoclonal antibody.

14. The method as claimed in claim 12, wherein the immunological test uses at least one anti-PVL monoclonal antibody.

15. The method as claimed in claim 11, further comprising determining whether the PVL-producing *Staphylococcus aureus* are methicillin-resistant (MRSA) or methicillin-sensitive (MSSA) when the PVL is detected in the biological sample.

16. The method as claimed in claim 12, further comprising determining whether the PVL-producing *Staphylococcus aureus* are methicillin-resistant (MRSA) or methicillin-sensitive (MSSA) when the PVL is detected in the biological sample.

17. The method as claimed in claim 13, further comprising determining whether the PVL-producing *Staphylococcus aureus* are methicillin-resistant (MRSA) or methicillin-sensitive (MSSA) when the PVL is detected in the biological sample.

18. The method as claimed in claim 14, further comprising determining whether the PVL-producing *Staphylococcus*

*aureus* are methicillin-resistant (MRSA) or methicillin-sensitive (MSSA) when the PVL is detected in the biological sample.

19. The method as claimed in claim 11, wherein the acid is $KH_2PO_4$.

20. The method as claimed in claim 1, wherein the pretreatment consists essentially of heating the biological sample at a temperature of between 60 and 100° C. for a period of more than 10 minutes.

21. The method as claimed in claim 11, wherein the pretreatment further comprises heating at a temperature of between 60 and 100° C. for a period of at least 10 minutes.

22. The method as claimed in claim 1, wherein the immunological test is lateral flow immunochromatography.

23. The method as claimed in claim 11, wherein the immunological test is lateral flow immunochromatography.

* * * * *